United States Patent [19]

Coquelet et al.

[11] Patent Number: 4,785,008
[45] Date of Patent: Nov. 15, 1988

[54] N-SUBSTITUTED 2-AMINO-THIAZOLES, PROCESS FOR THEIR PREPARATION AND THEIR THERAPEUTIC APPLICATION

[75] Inventors: Claude Coquelet, St Gely du Fesc; Daniel Sincholle, St Mathieu de Treviers; Claude Bonne, Castelnau le Lez; Alain Alazet, Agde, all of France

[73] Assignee: Laboratoires Chauvin-Blache, Montpellier, France

[21] Appl. No.: 855,411

[22] Filed: Apr. 24, 1986

[30] Foreign Application Priority Data

Apr. 30, 1985 [FR] France ............................. 85 06568

[51] Int. Cl.$^4$ .................. C07D 277/42; C07D 417/12; A61K 31/425; A61K 31/445
[52] U.S. Cl. .................................... 514/342; 514/370; 546/209; 548/193
[58] Field of Search ................ 548/193; 514/370, 342; 546/209

[56] References Cited

U.S. PATENT DOCUMENTS 3,228,888 1/1966 Spivack ............................... 548/193
3,467,666 9/1969 Dexter ................................. 548/193

FOREIGN PATENT DOCUMENTS 2309251 9/1973 Fed. Rep. of Germany.
1302433 7/1962 France.
2022085 12/1979 United Kingdom.

Primary Examiner—Robert Gerstl
Attorney, Agent, or Firm—Young & Thompson

[57] ABSTRACT

The subject of the invention is N-substituted 2-amino-thiazoles of formula

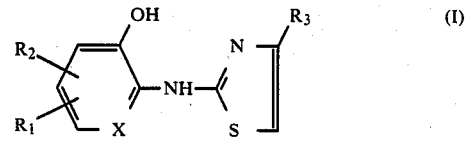

in which:
X is a C—H group or a nitrogen atom,
$R_1$ and $R_2$ are, independently of each other, a hydrogen atom, a halogen atom or an alkyl, alkoxy, alkylthio, alkenyloxy, cycloalkyl, trifluoromethyl, nitro, amino, ($C_1$-$C_6$ alkyl)amino or di($C_1$-$C_6$ alkyl)-amino radical, and
$R_3$ is a hydrogen atom, a —$CH_2$—OH group or a —$COOR_4$ group, $R_4$ being a hydrogen atom or an alkyl group, and also the pharmaceutically acceptable salts thereof.

These compounds have an anti-inflammatory and anti-allergic activity and can be used in therapy, especially in the ocular field.

8 Claims, No Drawings

N-SUBSTITUTED 2-AMINO-THIAZOLES, PROCESS FOR THEIR PREPARATION AND THEIR THERAPEUTIC APPLICATION

The present invention relates to new N-substituted 2-aminothiazoles having anti-inflammatory and antiallergic activity. These compounds can be used, in particular, in the treatment of inflammatory phenomena, especially in the treatment of ocular inflammatory phenomena.

The ocular inflammatory response is a sequence of events induced by a lesion or irritation of the tissues of the eye. It results in an increase in the intraocular pressure, a leukocyte infiltration into the tissues and fluids of the eye, an increase in the protein level in the aqueous humour and uveitis.

Although the nature of the inflammatory response is extremely varied and its mediators are manifold (kinins, histamine, and the like), there is always a production of pro-inflammatory metabolites of arachidonic acid in the damaged tissue, namely, prostaglandins (PGs) and hydroxyeicosatetraenoic acids (HETEs). This production is increased by the infiltration of polymorphonuclear leukocytes (PMNs) to the site of the inflammation, which in turn produce PGs and HETEs during phagocytosis. The known biological effects of HETEs are, inter alia, chemokinestism and chemotactism as regards PMNs.

PGs and HETEs are metabolites of arachidonic acid, a $C_{20}$ fatty acid. They are synthesized by two distinct pathways:

the cyclooxygenase pathway leads successively to the endoperoxides $PGG_2$ and $PGH_2$, which are precursors of various series 2 PGs. Among the latter, $PGE_2$ and $PGI_2$ (prostacyclin) are especially vasodilatory.

the lipoxygenase pathway leads to non-cyclized mono- and dihydroxyeicosatetraenoic acids (HETEs) which are, for the most part, pro-inflammatory agents, like their precursors the corresponding hydroxyperoxylated acids (HPETEs). Thus, 5,12-diHETE or leukotriene $B_4$ ($LTB_4$) is the most powerful chemotactic agent known for human leukocytes. Metabolites of this pathway are involved, in addition, in allergic reactions such as asthma.

In contrast to the PGs, which have common precursors, $PGG_2$ and $PGH_2$, the products of lipoxygenase have different precursors:

12-HPETE in the platelets, synthesized through the action of a 12-lipoxygenase, leads to the formation of 12-HETE.

in the leukocytes, 5-HPETE and 15-HPETE are mainly involved, leading to 5-HETE, 5,12-diHETE and 15-HETE.

The search for therapeutic agents capable of counteracting the inflammatory reaction was directed towards the following pathways:

inhibition of the release of arachidonic acid by glucocorticoids. The major disadvantage of glucocorticoids is that of causing an increase in the intraocular pressure and promoting the appearance of glaucoma or a cataract.

inhibition of the cyclooxygenase pathway by non-steroid anti-inflammatories, such as aspirin, indomethacin or Tanderil. But recent experimental studies show that indomethacin increases the leukocyte infiltration into the aqueous humour: by inhibiting the cyclooxygenase pathway, it promotes the lipoxygenase pathway and consequently the release of chemotactic products.

Simultaneous inhibition of the 5-lipoxygenase and the cyclooxygenase pathway is capable of blocking the synthesis of the different pro-inflammatory mediators, as do glucocorticoids, but without causing the troublesome effects of the latter.

Furthermore, inhibition of the 5-lipoxygenase pathway is likely to block the synthesis of the peptide leukotrienes $LTC_4$ and its metabolite $LTD_4$ (formerly known by the name SRS-A), which perform an important pathophysiological role in immediate hypersensitivity reactions.

The present invention is based precisely on the discovery that certain 2-aminothiazoles inhibit both leukocyte lipoxygenase and the formation of platelet prostanoids. They hence counteract the development of the vascular phase of inflammation (involving HETEs).

The present invention relates thus to compounds of formula

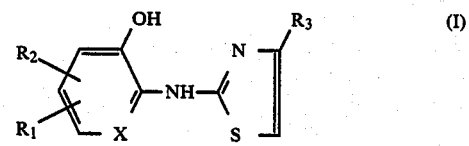

in which:

X is a C—H group or a nitrogen atom:

$R_1$ and $R_2$ are, independently of each other, a hydrogen atom, a halogen atom, a $C_1$–$C_{12}$ alkyl radical, a $C_1$–$C_6$ alkoxy radical, a $C_1$–$C_6$ alkylthio radical, a $C_2$–$C_6$ alkenyloxy radical, a $C_5$–$C_7$ cycloalkyl radical, a trifluoromethyl radical, a nitro group, an amino group, a ($C_1$–$C_6$ alkyl)amino group or a di($C_1$–$C_6$ alkyl)amino group, and $R_3$ denotes a hydrogen atom, a —$CH_2OH$ group or a —$COOR_4$ group, $R_4$ being a hydrogen atom or a $C_1$–$C_6$ alkyl group, and also the pharmaceutically acceptable salts thereof.

The present invention relates also to therapeutic compositions containing, as active principle, a compound of formula I or one of its pharmaceutically acceptable salts.

Pharmaceutically acceptable salts denotes addition salts formed by the compounds of formula (I) with pharmaceutically acceptable acids, and also the salts formed by the compounds of formula (I) having an acid group ($R_3$=COOH) with pharmaceutically acceptable bases.

"Addition salts with pharmaceutically acceptable acids" denote the salts which show the biological properties of the free bases, without having any adverse effect. These salts can be, in particular, those formed with inorganic acids such as hydrochloric acid, hydrobromic acid, sulphuric acid, nitric acid, phosphoric acid; acid salts of metals, such as disodium orthophosphate and monopotassium sulphate; and organic acids, such as formic acid, acetic acid, propionic acid, glycolic acid, oxalic acid, fumaric acid, lactic acid, succinic acid, tartaric acid and pamoic acid.

Similarly, "salts with pharmaceutically acceptable bases" denote the salts which do not modify the biological properties of the free acids. These salts can be, in particular, those formed with inorganic bases such as sodium hydroxide, potassium hydroxide, lithium hydroxide, calcium hydroxide and magnesium hydroxide, or organic bases such as glucamine, N-methylglucamine, N,N-dimethylglucamine, ethanolamine, diethanolamine, morpholine, N-methylmorpholine and tris(hydroxymethyl)methylamine.

The term "halogen" denotes fluorine, chlorine, bromine or iodine.

The alkyl groups preferably have from 1 to 6 carbon atoms.

A preferred class of compounds of formula I is that in which $R_1$ is a hydrogen atom, a halogen atom in position 5 or a $C_1$–$C_4$ alkyl group in position 4 or 5 and $R_2$ is a hydrogen atom, or alternatively in which $R_1$ and $R_2$ are $C_1$–$C_4$ alkyl groups in positions 3 and 5.

The compounds of formula I in which $R_3$ is a hydrogen atom or a —COOR$_4$ group, $R_4$ being an $C_1$–$C_6$ alkyl group, can be prepared by reaction of an N-substituted thiourea of formula

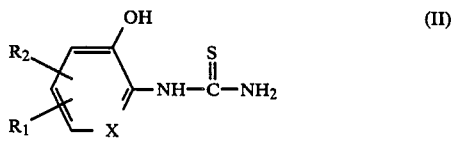

in which $R_1$, $R_2$ and X have the definition given above, with 1,2-dichloro-2-ethoxyethane, chloroacetaldehyde, chloroacetaldehyde diethyl acetal, 1,2-dichloroethyl acetate or a $C_1$–$C_6$ alkyl bromopyruvate.

The reaction of an N-substituted thiourea of formula II with, for example, chloroacetaldehyde diethyl acetal can be accomplished by bringing an alcoholic solution of equimolar amounts of reagents to reflux for 30 minutes to 24 hours in the presence of an acid catalyst such as hydrochloric acid or p-toluenesulphonic acid.

The thioureas of formula II can be prepared by the action of benzoyl thiocyanate on an amine of formula

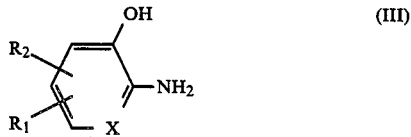

in which $R_1$, $R_2$ and X have the definition given above.

This reaction can be performed, for example, by slowly adding an acetone solution of amine of formula III to an acetone solution, brought to reflux, of benzoyl thiocyanate prepared in situ by a known process. After a brief period of refluxing, the condensation product is hydrolysed with an alkaline aqueous solution to lead to a derivative of formula II.

Compounds of formula I in which $R_3$ is a —COOH group can be obtained by saponification of the corresponding alkyl esters.

Compounds of formula I in which $R_3$ is a —CH$_2$OH group can be obtained by reduction of these esters, for example with lithium aluminium hydride.

The addition salts of the compounds of the invention with pharmaceutically acceptable acids can be prepared in the conventional manner, by reaction of the free bases with an acid or an acid salt, in particular in ethereal or alcoholic solution. The salts of the compounds having an acid group with bases are obtained by reaction of the acid with a base in one of the usual solvents.

Examples of compounds of formula I will be given below in Table I. The examples which follow illustrate the preparation of the compounds of formula I.

EXAMPLE 1

(a) Preparation of 1-(2-hydroxy-4-methylphenyl)-2-thiourea 0.2 mole of benzoyl chloride is added dropwise to a solution of 0.22 mole of ammonium thiocyanate in 100 ml of anhydrous acetone. The mixture is boiled to reflux for 5 minutes after the addition is complete, and a solution of 0.2 mole of 6-amino-m-cresol in 50 ml of anhydrous acetone is then added dropwise so as to maintain gentle refluxing. Stirring and heating are continued for 5 minutes after the addition, the reaction mixture is poured into 1.5 l of ice-cold water, and the crystals obtained are drained and suspended in 300 ml of 10% strength sodium hydroxide solution. The mixture is is brought to boiling for 10 minutes, and the solution is filtered on glass wool and acidified strongly with concentrated hydrochloric acid. The solution is brought back to pH 8 with ammonia solution. The crystals which precipitate on cooling are drained, washed with water and recrystallized in ethanol. (M.p. 175°–7° C.) Yld: 65%.

(b) Preparation of 2-(2-hydroxy-4-methylphenyl)aminothiazole hydrochloride

A mixture of the thiourea obtained in (a) (0.1 mole), chloroacetaldehyde diethyl acetal (0.1 mole) and p-toluenesulphonic acid (0.015 mole) in 300 ml of 70° strength alcohol is brought to reflux for 12 hours. After evaporation of the solvent under vacuum, the oily residue is ground in aqueous sodium acetate solution. The organic phase is extracted with ether, and the ethereal solution is washed with water, dried over anhydrous sodium sulphate and the decolourized with charcoal. After filtration, the ethereal solution is saturated with a stream of dry hydrochloric acid gas. The crystals formed are isolated and then recrystallized in an ethanol/ether mixture. (M.p. 184°–6° C.) Yld: 50%.

EXAMPLE 2

Preparation of 2-(2-hydroxy-4-methylphenyl)amino-4-carbethoxy-thiazole hydrobromide 0.065 mole of 1-(2-hydroxy-4-methylphenyl)-2-thiourea and 0.077 mole of ethyl bromopyruvate in 100 ml of 95° strength ethanol are brought to reflux for 3 hours. After evaporation of the solvent, crystallization of the residual oil is induced in diethyl ether. The product is then recrystallized in an ethanol/ether mixture. (M.p. 158°–60° C.) yield: 65%.

EXAMPLE 3

2-(2-hydroxy-4-methylphenyl)amino-4-hydroxymethyl-thiazole.

0.02 mole of the product obtained in Example 2 is added in small portions at room temperature to a suspension of 0.05 mole of lithium aluminium hydride in 100 ml of anhydrous THF. Stirring is maintained for 1 hour at room temperature, the mixture is cooled and the excess hydride destroyed by adding water, the solid is allowed to drain and the filtrate is evaporated under vacuum on a water bath. The oily residue is then crystallized in ether and recrystallized in a methanol/ether mixture. (M.p. 188°–90° C.). Yield: 30%.

EXAMPLE 4

2-(2-hydroxy-4-methylphenyl)aminothiazole-4-carboxylic acid hydrochloride.

0.03 mole of 2-(2-hydroxy-4-methylphenyl)amino-4-carbethoxythiazole hydrobromide in 100 ml of 1N sodium hydroxide solution is brought to reflux for 2 hours. After the mixture is cooled, the hydrochloride of the acid is precipitated by adding concentrated hydrochloric acid. The product is recrystallized in ethanol. (M.p. 248°–50° C.). Yield: 60%.

which 50% inhibits $LTC_4$ tracer formation ($IC_{50}$) is deduced.

By way of example, a number of results are given in Table II.

1.2—Inhibition of the metabolism of [$^{14}C$]arachidonate in rabbit platelets

Methods

Preparation of a platelet-rich plasma (PRP)

12 ml of blood are withdrawn nitracardially into ACD (anticoagulant consisting of an aqueous solution containing 0.27 g of citric acid, 0.5 g of disodium citrate and 0.02 g of glucose for 20 ml of water) in a proportion

TABLE I

| Compound No. | $R_1$ | $R_2$ | X | $R_3$ | Yield (%) | Melting point (°C.) | Recrystallization solvent | Salt |
|---|---|---|---|---|---|---|---|---|
| 1 | H | H | CH | H | 40 | 159–61 | Acetone/ethanol | Hydrochloride |
| 2 | 5-Cl | H | CH | H | 30 | 172–4 | Acetone | Hydrochloride |
| 3 | 4-$CH_3$ | H | CH | H | 50 | 184–6 | Ethanol | Hydrochloride |
| 4 | 5-$CH_3$ | H | CH | H | 40 | 162–4 | Ethanol | Hydrochloride |
| 5 | 4-$CH_3$—C($CH_3$)($CH_3$) | H | CH | H | 25 | 172–4 | Acetone/methanol | Hydrochloride |
| 6 | 3-$CH_3$ | 5-$CH_3$ | CH | H | 40 | 209–11 | Ethanol | Hydrochloride |
| 7 | H | H | N | H | 20 | 238–40 | Methanol/ether | Hydrochloride |
| 8 | 4-$CH_3$ | H | CH | —$COOC_2H_5$ | 65 | 158–60 | Ethanol/ether | Hydrobromide |
| 9 | 4-$CH_3$ | H | CH | —$CH_2OH$ | 30 | 188–90 | Ether | |
| 10 | 4-$CH_3$ | H | CH | —COOH | 60 | 248–50 | Ethanol | Hydrochloride |
| 11 | 5-$CH_3$ | H | CH | —COOH | 70 | 253–55 | Ethanol | Hydrochloride |
| 12 | 5-$OCH_3$ | H | CH | H | 54 | 180–82 | Methanol | |

Results of the pharmacological and toxicological studies which demonstrate the properties of the compounds of formula I are given below.

1—Biochemical pharmacology "in vitro"

1.1—Inhibition of the lipoxygenase of circulating human leukocytes (PMNs), by radioimmunoassay of $LTC_4$ Methods Preparation of a leukocyte suspension Heparinized human blood is sedimented for 1 hour at 37° C. in sterile saline solution containing 4.5% of Dextran T 500. The upper, leukocyte-rich phase, is collected, deposited on Ficoll-Paque (7:3 v/v) and then centrifuged (20 minutes, 400×g, 4° C.). The centrifugation pellet is treated with 0.75% strength $NH_4Cl$ to lyse the red cells. After centrifugation (20 minutes, 400×g, 4° C.), supernatent is removed and the pellet is resuspended in Dulbecco's PBS buffer containing 1 mM calcium chloride. The volume of the suspension is adjusted to obtain the desired leukocyte concentration.

Radioimmunoassay of $LTC_4$

The leukocyte suspension is pre-incubated for 2 minutes with the test compound of formula I, and then incubated for 8 minutes at 37° C. in the presence of calcium ionophore A23187 (0.25 $\mu$M). The incubation is blocked by adding one volume of ice-cold water, and the suspension is centrifuged (15 minutes, 1500×g, 4° C.). Aliquots of the supernatent are then subjected to radioimmunoassay (New England Nuclear Kit).

Results

The percentage inhibition of the 5-lipoxygenase pathway is measured in terms of the concentration of each compound. From these curves, the concentration of 1 volume of ACD for 6 volumes of blood. The mixture is centrifuged (10 minutes, 200×g, 20° C.), and the supernatent (PRP) collected and centrifuged again (15 minutes, 1500×g, 20° C.). The platelet pellet is washed in buffer I [NaCl, 8 g/l; Tris, 1.21 g/l; KCl, 0.2 g/l; gelatin, 2.5 g/l; this mixture is heated to 90° C. to dissolve the gelatin, and then glucose, 1 g/l, and ethylene glycol bis($\beta$-aminoethyl ether) N,N,N',N'-tetraacetic acid or EGTA, 0.075 g/l, are added]. The suspension is centrifuged (15 minutes, 1500×g, 20° C.) and the pellet taken up in buffer II (NaCl, 8 g/l; Tris, 1.21 g/l; KCl, 0.2 g/l; $CaCl_2$, 0.145 g/l; $MgCl_2$, 0.2 g/l; gelatin, 2.5 g/l; the mixture is brought to 90° C., glucose, 1 g/l, is added and the pH is adjusted to 7.4 with 0.1N HCl).

Metabolism of [$^{14}C$]arachidonate

The platelet suspension (0.4 ml/tube) is preincubated for 10 minutes at 37° C., either with 10 $\mu$l of DMSO (control), or with varied concentrations of test compounds dissolved in 10 $\mu$l of DMSO.

The incubation is carried out in the presence of [$^{14}C$]arachidonate (1 $\mu$g, 0.2 $\mu$Ci) distributed in 0.1 ml of buffer II, and the incubation is then blocked after 15 minutes with 50 $\mu$l of citric acid and 250 $\mu$l of saturated NaCl.

After extraction with ethyl acetate, the metabolites of [$^{14}C$]arachidonate are separated by thin layer chromatography and quantified using a radio-scanner.

Results

The percentage inhibition of the prostanoid pathways is estimated by measuring the disappearance of thromboxane $B_2$ ($TXB_2$) in terms of the concentration of each compound.

Results corresponding to 50 μM and 100 μM of compounds of formula I are given by way of example in Table II.

TABLE II

| Compound No. | Inhibition of LTC$_4$ in human PMNs IC$_{50}$ (× 10$^{-6}$ M) | Inhibition of TXB$_2$ in rabbit platelets (%) | |
|---|---|---|---|
| | | 50 μM | 100 μM |
| 1 | 1.2 | 34 | 91 |
| 2 | 0.3 | 100 | 100 |
| 3 | 0.33 | 100 | 100 |
| 4 | 0.25 | 68 | n.d. |
| 5 | 1.6 | 76 | n.d. |
| 6 | 0.2 | 70 | n.d. |
| 7 | n.d. | 36 | 36 |

(n.d.: not determined)

2—Functional pharmacology

Anti-inflammatory activity measured by the inhibition of protein influx into the anterior chamber of the eye after corneal paracentesis.

This activity is measured according to the technique of K. Masuda et al. (Bibl. Anat., 1977, 6, 99–104).

The effect of various concentrations of each compound is measured on 6 eyes of albino New Zealand rabbits.

The results below are given by way of example.

| Compound | Dose mg/100 ml | Inhibition (%) |
|---|---|---|
| Indomethacin | 1 | 80 |
| Compound n° 3 | 0.1 | 20 |
| | 0.5 | 35 |
| | 1 | 50 |

3—Acute toxicity

The rats used are of Wistar strain of average weight 150 g.

The LD$_{50}$ is determined after 14 days of observation.

The results below give the LD$_{50}$ values for the compound 3 of the invention, together with the 5% confidence interval.

| | | LD$_{50}$ (mg/kg) |
|---|---|---|
| Male rat | IV | 51 ± 2 |
| | PO | 2950 ± 96 |
| Female rat | IV | 51 ± 2 |
| | PO | 2350 ± 90 |

The compounds according to the present invention can be used in the treatment of conditions which contain an inflammatory component, and in particular:
- in ophthalmology, for the treatment of post-traumatic inflammations, allergic conjunctivitis, bacterial conjunctivitis, viral conjunctivitis, blepharitis, uveitis-iridocyclitis, keratitis, keratoconjunctivitis, retinitis and Gougerot-Sjögren's syndrome,
- in ENT, for the treatment of allergic and infectious rhinitis, rhinopharyngitis, tonsilitis, otitis, stomatitis, gingivitis, alveolitis, laryngitis, epiglottitis and parotiditis,
- in dermatology, in the treatment of psoriasis, irritative and allergic dermititis, surges of inflammation in collagen diseases (lupus, scleroderma, polyarthritis, dermatomyositis, etc.), ulcers and cutaneous ulceration, inflammatory acne, folliculitis and vasculitis,
- in pneumology, in the treatment of bronchitis, alveolitis, pleurisy and pneumopathies,
- in proctology, in the treatment of haemorrhoids and anal fistulae,
- in rheumatology, in the treatment of osteoarthritis, acute or chronic polyarthritis, lumbago, sciatica, cervical pain, tendinitis, post-traumatic inflammations and muscular trauma,
- in gynaecology, in the treatment of bartholinitis, vulvovaginitis, prostatitis, urethritis, cystitis, orchitis and balanitis,
- as well as in the treatment of phlebitis, lymphangitis and pericarditis.

The therapeutic compositions according to the invention can be administered topically, orally or parenterally (including by intra-articular administration) to man or animals.

They can be in the form of solid, semi-solid or liquid preparations. As examples, there may be mentioned tablets, gelatin capsules, suppositories, injectable solutions or suspensions, ointments, oily or aqueous eyewashes, mouth-washes, nasal solutions and ear-drops, as well as slow-release forms.

In these compositions, the active principle is generally mixed with one or more of the customary pharmaceutically acceptable excipients which are well known to those skilled in the art.

The therapeutic compositions which can be administered topically can contain, in particular, from 0.1 to 5% by weight of active principle.

The therapeutic compositions which can be administered orally or parenterally can contain, in particular, from 1 to 60% by weight of active principle.

The amount of active principle administered naturally depends on the patient who is being treated, the administration route and the severity of the disease. However, for oral or parenteral administration, from approximately 0.25 to 5 mg/kg/day approximately can be administered, equivalent to 17.5 to 350 mg/day, and preferably from 25 to 250 mg/day, for a man weighing 70 kg.

The compounds of formula I and their addition salts with pharmaceutically acceptable acids can also be used, by virtue of their antioxidant properties, as preservatives and antioxidants for human and animal foodstuffs.

Examples of therapeutic compositions according to the invention are given below.

| Solution | |
|---|---|
| 2-(2-Hydroxy-4-methylphenyl)aminothiazole hydrochloride | 0.1% |
| Isotonic solution | qs 100 |
| ENT topical aerosol | |
| 2-(2-Hydroxy-4-methylphenyl)aminothiazole hydrochloride | 0.2% |
| Ethyl alcohol, 95° strength | 2% |
| Aromatized excipient | qs 100 |
| Pressurization under nitrogen pressure | |
| Ointment | |
| 2-(2-Hydroxy-4-methylphenyl)aminothiazole hydrochloride | 5% |
| Liquid paraffin | 20% |
| Vaseline | 75% |
| Tablet | |
| 2-(2-Hydroxy-4-methylphenyl)aminothiazole hydrochloride | 0.100 g |
| Maize starch | 0.075 g |
| Magnesium stearate | 0.020 g |
| Colloidal silicic acid | 0.005 g |
| Gelatin capsule | |
| 2-(2-Hydroxy-4-methylphenyl)aminothiazole | 0.100 g |

| -continued | |
|---|---|
| hydrochloride | |
| Magnesium stearate | 0.020 g |
| Suppository | |
| 2-(2-Hydroxy-4-methylphenyl)aminothiazole hydrochloride | 0.200 g |
| Semi-synthetic glycerides qs approximately | 1.700 g |

We claim:

1. A compound of the formula

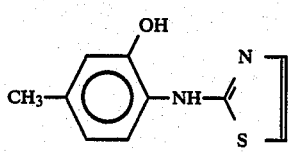

and pharmaceutically acceptable salts thereof.

2. A therapeutic composition having an anti-inflammatory activity comprising an effective amount of a compound as claimed in claim 1 in admixture with a pharmaceutically acceptable excipient.

3. A therapeutic composition as claimed in claim 2, which is in a form which can be administered topically.

4. A therapeutic composition as claimed in claim 2, which is in a form which can be administered orally.

5. A therapeutic composition as claimed in claim 2, which is in a form which can be administered parenterally.

6. A therapeutic composition having an inhibitory activity of lipoxygenase and on the formation of platelet prostanoids, comprising an effective amount of a compound as claimed in claim 1 in admixture with a pharmaceutically acceptable excipient.

7. A process for the treatment of inflammatory phenonema, which comprises administering to a human in need thereof an effective amount of a compound of the formula

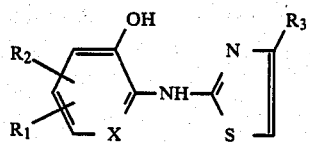

in which:

X is a C—H group or a nitrogen atom, $R_1$ and $R_2$ are each selected from the group consisting of hydrogen, halogen, $C_1$–$C_{12}$ alkyl, $C_1$–$C_6$ alkoxy, $C_1$–$C_6$ alkylthio, $C_2$–$C_6$ alkenyloxy, $C_5$–$C_7$ cycloalkyl, trifluoromethyl, nitro, amino, ($C_1$–$C_6$ alkyl)amino and di($C_1$–$C_6$ alkyl) amino; and $R_3$ is selected from hydrogen, —$CH_2OH$ and —$COOR_4$, $R_4$ being selected from hydrogen and $C_1$–$C_6$ alkyl.

8. A process for the treatment of inflammatory phenomena, which comprises administering to a human in need thereof an effective amount of a compound of the formula

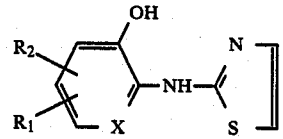

in which:

X is a C—H group or a nitrogen atom, and $R_1$ and $R_2$ are each selected from the group consisting of hydrogen, halogen, $C_1$–$C_{12}$ alkyl, $C_1$–$C_6$ alkoxy, $C_1$–$C_6$ alkylthio, $C_2$–$C_6$ alkenyloxy, $C_5$–$C_7$ cycloalkyl, trifluoromethyl, nitro, amino, ($C_1$–$C_6$ alkyl)amino and di($C_1$–$C_6$ alkyl)amino; and pharmaceutically acceptacle salts thereof.

* * * * *